US009223011B2

(12) United States Patent
Miyachi

(10) Patent No.: US 9,223,011 B2
(45) Date of Patent: Dec. 29, 2015

(54) ULTRASONIC SIGNAL PROCESSING DEVICE AND ULTRASONIC SIGNAL PROCESSING METHOD

(71) Applicant: FUJIFILM Corporation, Tokyo (JP)

(72) Inventor: Yukiya Miyachi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/527,361

(22) Filed: Oct. 29, 2014

(65) Prior Publication Data

US 2015/0049582 A1 Feb. 19, 2015

Related U.S. Application Data

(63) Continuation of application No. PCT/JP2013/063760, filed on May 17, 2013.

(30) Foreign Application Priority Data

May 25, 2012 (JP) .................................. 2012-119912

(51) Int. Cl.
*G01S 7/52* (2006.01)
*G01N 29/07* (2006.01)
(Continued)

(52) U.S. Cl.
CPC ........... *G01S 7/52017* (2013.01); *A61B 8/4483* (2013.01); *G01N 29/0654* (2013.01); *G01N 29/0672* (2013.01); *G01N 29/07* (2013.01); *G01S 7/52049* (2013.01); *G01S 7/52053* (2013.01); *G01S 7/52074* (2013.01);
(Continued)

(58) Field of Classification Search
CPC .... A61B 8/4483; A61B 8/06; G01S 7/52049; G01S 7/52074; G01S 7/52085; G01S 7/52017; G01S 7/52053; G01S 15/02; G01N 29/0672; G01N 29/07; G01N 29/0654
See application file for complete search history.

(56) References Cited

U.S. PATENT DOCUMENTS 8,663,115 B2 * 3/2014 Yamamoto ........... A61B 8/4477
600/440
2010/0130861 A1 5/2010 Shimazaki
(Continued)

FOREIGN PATENT DOCUMENTS

JP 7-100135 A 4/1995
JP 7-111993 A 5/1995
(Continued)

OTHER PUBLICATIONS

International Search Report, issued in PCT/JP2013/063760, dated Jun. 11, 2013.
(Continued)

*Primary Examiner* — Daniel Pihulic
(74) *Attorney, Agent, or Firm* — Birch, Stewart, Kolasch & Birch, LLP

(57) ABSTRACT

An ultrasonic signal processing method includes: measuring a sound velocity in a subject according to transmission/reception data acquired in ultrasonic transmission of M times (M is an integer equal to or greater than 1 and less than N) along different transmission focus lines among ultrasonic transmission of N times (N is an integer equal to or greater than 2) along multiple transmission focus lines in a case where ultrasonic transmission is sequentially performed at least one time on each of multiple transmission focus lines to create an ultrasonic image for one frame.

20 Claims, 11 Drawing Sheets

(51) Int. Cl.
*G01S 15/02* (2006.01)
*G01N 29/06* (2006.01)
*A61B 8/00* (2006.01)
*A61B 8/06* (2006.01)

(52) U.S. Cl.
CPC .............. *G01S 7/52085* (2013.01); *G01S 15/02* (2013.01); *A61B 8/06* (2013.01)

(56) References Cited

U.S. PATENT DOCUMENTS

| | | | | |
|---|---|---|---|---|
| 2011/0077519 | A1* | 3/2011 | Katsuyama | A61B 8/08 600/443 |
| 2012/0203109 | A1* | 8/2012 | Tanabe | A61B 8/463 600/447 |
| 2012/0220871 | A1* | 8/2012 | Yamamoto | A61B 8/4477 600/441 |
| 2012/0238874 | A1* | 9/2012 | Miyachi | A61B 8/5269 600/443 |
| 2012/0245467 | A1* | 9/2012 | Miyachi | G01S 7/52038 600/447 |
| 2012/0245468 | A1* | 9/2012 | Miyachi | G01S 7/52036 600/447 |
| 2012/0259225 | A1* | 10/2012 | Tashiro | A61B 8/14 600/443 |
| 2013/0041262 | A1* | 2/2013 | Katsuyama | G01S 7/52049 600/447 |
| 2013/0296706 | A1* | 11/2013 | Katsuyama | A61B 8/08 600/447 |
| 2013/0303912 | A1* | 11/2013 | Katsuyama | A61B 8/08 600/447 |
| 2015/0049582 | A1* | 2/2015 | Miyachi | A61B 8/4483 367/7 |
| 2015/0065885 | A1* | 3/2015 | Miyachi | A61B 8/4483 600/459 |
| 2015/0196280 | A1* | 7/2015 | Yamamoto | A61B 8/4461 600/440 |

FOREIGN PATENT DOCUMENTS

| | | |
|---|---|---|
| JP | 8-154930 A | 6/1996 |
| JP | 2009-61086 A | 3/2009 |
| JP | 2010-124946 A | 6/2010 |
| JP | 2010-207490 A | 9/2010 |

OTHER PUBLICATIONS

Written Opinion of the International Searching Authority, issued in PCT/JP2013/063760, dated Jun. 11, 2013.

* cited by examiner

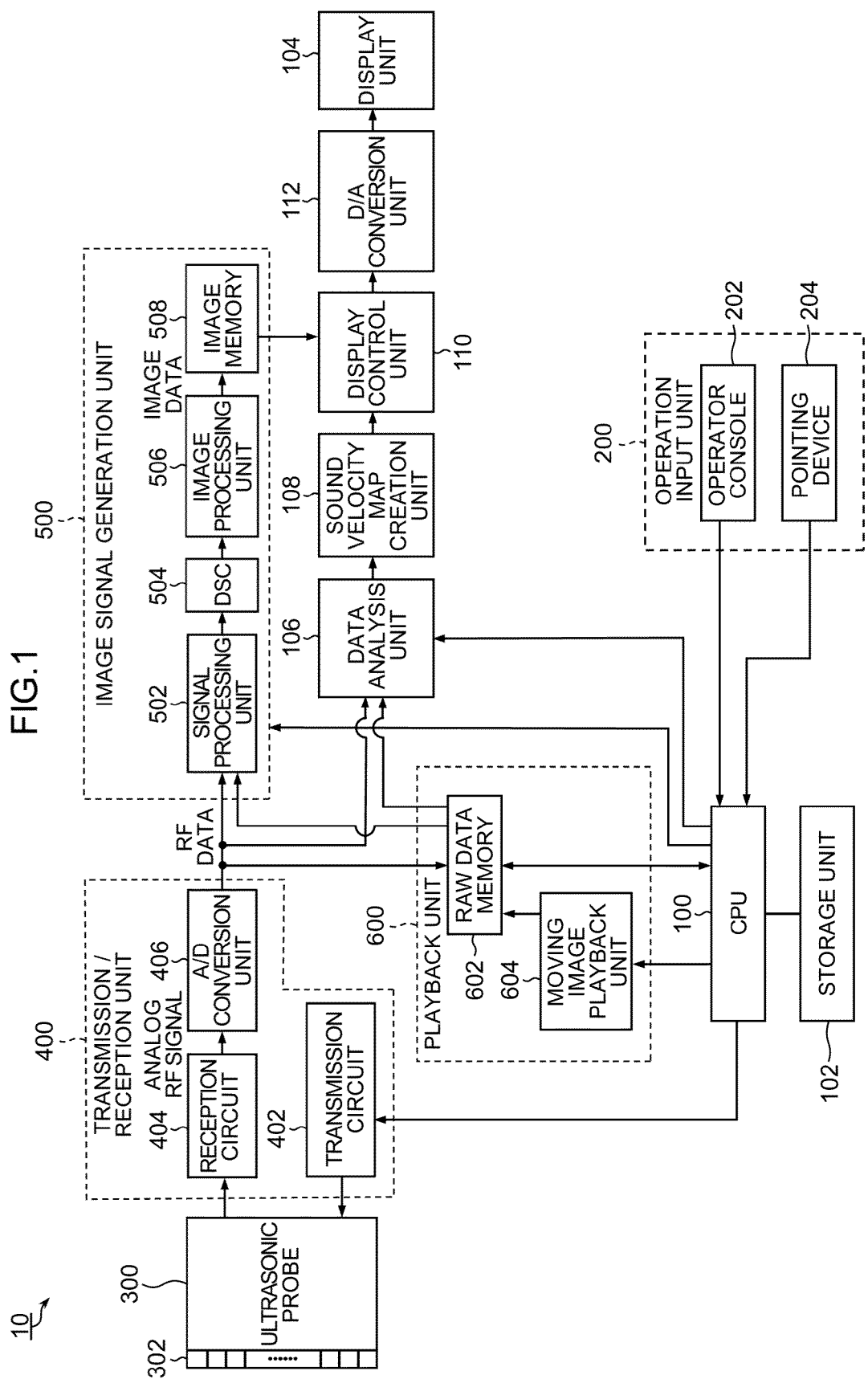

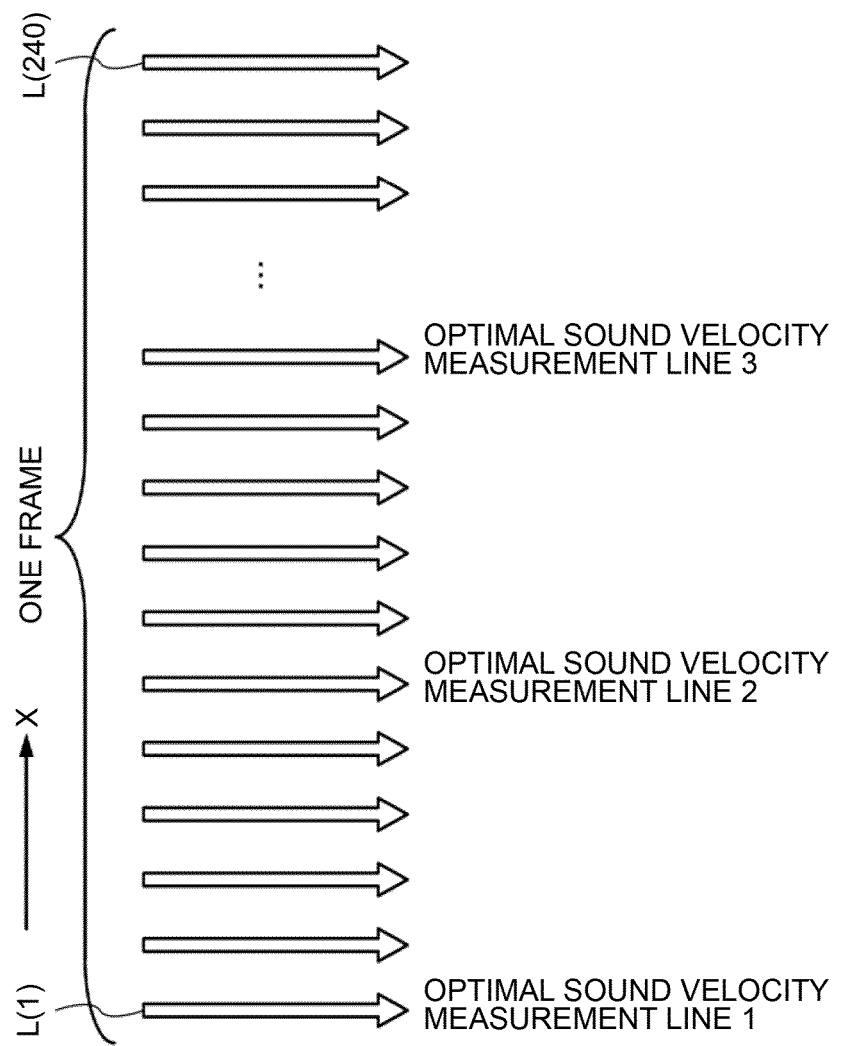

ULTRASONIC SIGNAL PROCESSING DEVICE AND ULTRASONIC SIGNAL PROCESSING METHOD

CROSS-REFERENCE TO RELATED APPLICATIONS

This application is a Continuation of PCT International Application No. PCT/JP2013/063760 filed on May 17, 2013, which claims priority under 35 U.S.C §119(a) to Japanese Patent Application No. 2012-119912 filed on May 25, 2012. Each of the above applications is hereby expressly incorporated by reference, in their entirety, into the present application.

BACKGROUND OF THE INVENTION

1. Field of the Invention

The presently disclosed subject matter relates to an ultrasonic signal processing device and an ultrasonic signal processing method, and particularly relates to an ultrasonic signal processing device and an ultrasonic signal processing method that scan an ultrasonic wave in a subject, determine the sound velocity in the subject and create an ultrasonic image.

2. Description of the Related Art

Japanese Patent Application Laid-Open No. H07-100135 (PTL 1) discloses that a frame rate is improved by performing transmission and reception for tomogram images (B mode) once after Doppler transmission and reception during Doppler cycle period Td (paragraphs [0019] and [0020]).

Japanese Patent Application Laid-Open No. 2010-124946 (PTL 2) discloses that elastic-image ultrasonic transmission and reception E1, E2, E3, E4, . . . are performed at intervals of time t, and B-mode-image ultrasonic transmission and reception B1, B2, B3, . . . to acquire an echo signal that creates a B-mode image are performed during the elastic-image ultrasonic transmission and reception (paragraphs [0033] and [0036]).

Japanese Patent Application Laid-Open No. H07-111993 (PTL 3) discloses that, in a region of interest, a scanning procedure is controlled so as to acquire two-dimensional bloodstream image data and tomographic image data alternately every multiple scanning lines, and a time lag is reduced between two images (paragraph [0030]).

SUMMARY OF THE INVENTION

In general, in a case where a B-mode image in a subject is created, a position and direction of ultrasonic transmission and reception are changed, and a strength of an ultrasonic echo is found every position and direction of the transmission and reception. Subsequently, by displaying a bright spot of brightness corresponding to the strength of the ultrasonic echo on a position corresponding to a distance to a reflection source of the ultrasonic echo, the B-mode image is created.

Meanwhile, a similar ultrasonic scan is performed even when a distribution of sound velocity in the subject is measured, but beam forming is performed while the sound velocity value of reception focus is changed every position and direction of the ultrasonic transmission and reception. Therefore, the measurement of the distribution of sound velocity has a problem of taking time as compared with a scan for creating the B-mode image. For example, in a case where the scan is implemented while changing the sound velocity value at 20 m/s intervals within a range of 1,440 m/s to 1,640 m/s, measurement processing of the sound velocity value takes processing time about 11 times B-mode image creation. Therefore, in a case where the sound velocity value is measured in real time and displayed while creating and displaying the B-mode image, there is a problem that the frame rate of the B-mode image decreases.

PTLs 1 to 3 are not to solve a decrease in the frame rate, which is caused when the creation of the B-mode image and the measurement of sound-velocity distribution are performed in parallel.

The presently disclosed subject matter is made in view of such conditions, and it is an object to provide an ultrasonic signal processing device and an ultrasonic signal processing method that can implement a scan for creating an ultrasonic image and a scan for measuring sound velocity distribution in parallel without decreasing the frame rate of an ultrasonic image.

To solve the above-mentioned problem, an ultrasonic signal processing device according to the first mode of the presently disclosed subject matter includes: an ultrasonic probe including multiple elements configured to transmit an ultrasonic wave to a subject, receive an ultrasonic wave reflected by the subject and output an ultrasonic detection signal; a transmission/reception data acquisition unit configured to acquire transmission/reception data by controlling the ultrasonic probe, sequentially transmitting an ultrasonic wave into the subject along multiple transmission focus lines and receiving the ultrasonic wave reflected by the subject; and a sound velocity measurement unit configured to measure sound velocity in the subject according to transmission/reception data acquired in ultrasonic transmission of M times (M is an integer equal to or greater than 1 and less than N) along different transmission focus lines among ultrasonic transmission of N times (N is an integer equal to or greater than 2) along the multiple transmission focus lines when ultrasonic transmission is sequentially performed at least one time on each of the multiple transmission focus lines to create an ultrasonic image for one frame.

According to the first mode, by assigning a scanning line for sound velocity measurement only to part of scanning lines for creation of an ultrasonic image (B-mode image), it is possible to calculate and display the sound velocity value in the subject in real time while displaying the ultrasonic image.

The ultrasonic signal processing device according to the second mode of the presently disclosed subject matter further includes: an ultrasonic image creation unit configured to create an ultrasonic image in the subject according to the transmission/reception data acquired by the transmission/reception data acquisition unit; and a display unit configured to display the ultrasonic image, in addition to the first mode.

The ultrasonic signal processing device according to the third mode of the presently disclosed subject matter is configured such that, when the ultrasonic image creation unit creates an ultrasonic image of N consecutive frames, the sound velocity measurement unit makes positions of transmission focus lines for a measurement of the sound velocity in the subject different every frame, in the second mode.

The ultrasonic signal processing device according to the fourth mode of the presently disclosed subject matter further includes: a sound velocity holding unit configured to hold a sound velocity for the N frames measured when the ultrasonic image for the N consecutive frames is created by the ultrasonic image creation unit, at least while the ultrasonic image for the N frames is created and displayed; and a sound velocity image creation unit configured to create a sound velocity image showing a sound velocity distribution in the subject by complementing (adding) the sound velocity for the N frames held in the sound velocity holding unit, in the third mode.

The ultrasonic signal processing device according to the fifth mode of the presently disclosed subject matter is configured such that the sound velocity image creation unit creates an optimal sound velocity value image showing an optimal sound velocity value in the subject and a local sound velocity value image showing a local sound velocity value of each region in the subject by complementing the sound velocity for the N frames held in the sound velocity holding unit, in the fourth mode.

The ultrasonic signal processing device according to the sixth mode of the presently disclosed subject matter is configured such that the display unit displays the sound velocity image together with the ultrasonic image according to an operation input from an operator in the fourth or fifth mode.

In the fourth to sixth modes, the position of the transmission focus line for measurement of sound velocity in N consecutive frames is made different every frame, and the sound velocity acquired in this transmission focus line is added. By this means, it is possible to create and display the sound velocity image in which a resolution in a scanning direction of ultrasonic waves is higher and the time lag with the ultrasonic image is smaller.

The ultrasonic signal processing device according to the seventh mode of the presently disclosed subject matter is configured such that, according to an operation input from an operator, the display unit selects and displays at least one of an optimal sound velocity value image subjected to a two-dimensional imaging of an optimal sound velocity value, a local sound velocity value image subjected to a two-dimensional imaging of a local sound velocity value every region in the subject and the ultrasonic image, in the fifth or sixth mode.

The ultrasonic signal processing device according to the eighth mode of the presently disclosed subject matter is configured such that: the sound velocity measurement unit calculates an optimal sound velocity value in the subject according to the transmission/reception data acquired in the ultrasonic transmission of M times; and the transmission/reception data acquisition unit performs beam forming during the ultrasonic transmission and reception of N times, in the first to seventh modes.

The ultrasonic signal processing device according to the ninth mode of the presently disclosed subject matter is configured such that the transmission/reception data acquisition unit calculates a line between transmission lines of the M times by interpolation operation, using a pixel value acquired according to the transmission/reception data acquired by the ultrasonic transmission of M times, in the first to eights modes.

The ultrasonic signal processing device according to the tenth mode of the presently disclosed subject matter is designed such that the sound velocity is an optimal sound velocity value or a local sound velocity value, in the first mode.

The ultrasonic signal processing device according to the eleventh mode of the presently disclosed subject matter is configured such that the sound velocity measurement unit measures a local sound velocity value of each region in the subject according to an optimal sound velocity value in the subject, in the first to tenth modes.

An ultrasonic signal processing method according to the twelfth mode of the presently disclosed subject matter includes: a transmission/reception data acquisition step of acquiring transmission/reception data by controlling an ultrasonic probe including multiple elements configured to transmit an ultrasonic wave to a subject, receive an ultrasonic wave reflected by the subject and output an ultrasonic detection signal, sequentially transmitting an ultrasonic wave into the subject along multiple transmission focus lines and receiving the ultrasonic wave reflected by the subject; and a sound velocity measurement step of measuring sound velocity in the subject according to transmission/reception data acquired in ultrasonic transmission of M times (M is an integer equal to or greater than 1 and less than N) along different transmission focus lines among ultrasonic transmission of N times (N is an integer equal to or greater than 2) along the multiple transmission focus lines when ultrasonic transmission is sequentially performed at least one time on each of the multiple transmission focus lines to create an ultrasonic image for one frame.

The ultrasonic signal processing method according to the thirteenth mode of the presently disclosed subject matter further includes: an ultrasonic image creation step of creating an ultrasonic image in the subject according to the transmission/reception data acquired in the transmission/reception data acquisition step; and a display step of displaying the ultrasonic image on a display unit, in addition to the twelfth mode.

The ultrasonic signal processing method according to the fourteenth mode of the presently disclosed subject matter is configured such that, when an ultrasonic image of N consecutive frames is created in the ultrasonic image creation step, positions of transmission focus lines for a measurement of the sound velocity in the subject are made different every frame in the sound velocity measurement step of the thirteenth mode.

The ultrasonic signal processing method according to the fifteenth mode of the presently disclosed subject matter further includes: a sound velocity holding step of holding a sound velocity for the N frames measured when the ultrasonic image for the N consecutive frames is created in the ultrasonic image creation step, at least while the ultrasonic image for the N frames is created and displayed; and a sound velocity image creation step of creating a sound velocity image showing a sound velocity distribution in the subject by complementing (adding) the sound velocity for the N frames held in the sound velocity holding step, in the fourteenth mode.

The ultrasonic signal processing method according to the sixteenth mode of the presently disclosed subject matter is configured such that an optimal sound velocity value image showing an optimal sound velocity value in the subject and a local sound velocity value image showing a local sound velocity value of each region in the subject are created by complementing the sound velocity for the N frames held in the sound velocity holding step, in the sound velocity image creation step of the fifteenth mode.

The ultrasonic signal processing method according to the seventeenth mode of the presently disclosed subject matter further includes a step of displaying the sound velocity image together with the ultrasonic image by the display unit according to an operation input from an operator, in the fifteenth or sixteenth mode.

The ultrasonic signal processing method according to the eighteenth mode of the presently disclosed subject matter is configured such that, according to an operation input from an operator, the display unit selects and displays at least one of an optimal sound velocity value image subjected to a two-dimensional imaging of an optimal sound velocity value, a local sound velocity value image subjected to a two-dimensional imaging of a local sound velocity value every region in the subject and the ultrasonic image, in the sixteenth or seventeenth mode.

The ultrasonic signal processing method according to the nineteenth mode of the presently disclosed subject matter is configured such that: an optimal sound velocity value in the subject is calculated according to the transmission/reception data acquired in the ultrasonic transmission of M times in the sound velocity measurement step of the twelfth to eighteenth modes; and beam forming is performed during the ultrasonic transmission and reception of N times in the transmission/reception data acquisition step.

The ultrasonic signal processing method according to the twentieth mode of the presently disclosed subject matter is configured such that a line between transmission lines of the M times is calculated by interpolation operation, using a pixel value acquired according to the transmission/reception data acquired by the ultrasonic transmission of M times in the transmission/reception data acquisition step of the twelfth to nineteenth modes.

The ultrasonic signal processing method according to the twenty first mode of the presently disclosed subject matter is designed such that the sound velocity is an optimal sound velocity value or a local sound velocity value, in the twelfth to twentieth modes.

The ultrasonic signal processing method according to the twenty second mode of the presently disclosed subject matter is configured such that the local sound velocity value of each region in the subject is measured based on an optimal sound velocity value in the subject, in the sound velocity measurement step of the twelfth to twenty first modes.

According to the presently disclosed subject matter, by assigning a scanning line for sound velocity measurement to only a part of scanning lines for creating an ultrasonic image (B-mode image), it is possible to calculate and display a sound velocity value in a subject in real time while displaying an ultrasonic image.

BRIEF DESCRIPTION OF THE DRAWINGS

FIG. 1 is a block diagram illustrating an ultrasonic signal processing device according to an embodiment of the presently disclosed subject matter;

FIG. 5 is a diagram schematically illustrating ultrasonic scan processing according to the first embodiment of the presently disclosed subject matter;

DETAILED DESCRIPTION OF EXEMPLARY EMBODIMENTS

Figure 2A:
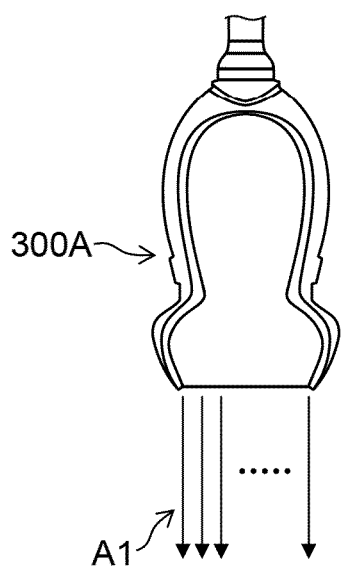
FIG. 2A is a diagram illustrating a linear ultrasonic probe.

In the following, embodiments of an ultrasonic signal processing device and ultrasonic signal processing method according to the presently disclosed subject matter are described according to the accompanying drawings.

Configuration of Ultrasonic Signal Processing Device

FIG. 1 is a block diagram illustrating an ultrasonic signal processing device according to an embodiment of the presently disclosed subject matter.

An ultrasonic signal processing device 10 illustrated in FIG. 1 is a device that transmits an ultrasonic beam from an ultrasonic probe 300 to a subject OBJ, receives an ultrasonic beam (ultrasonic echo) reflected by the subject OBJ and creates and displays an ultrasonic image from a detection signal of the ultrasonic echo (ultrasonic detection signal).

A CPU (Central Processing Unit) 100 controls each block of the ultrasonic signal processing device 10 according to an operation input from an operation input unit 200.

The operation input unit 200 is an input device configured to accept an operation input from an operator, and the operation input unit 200 includes an operator console 202 and a pointing device 204. The operator console 202 includes: a keyboard configured to accept an input of character information (for example, patient information); a display mode switching button configured to switch a display mode between a mode to display an amplitude image (B-mode image) alone and a mode to display a determination result of a local sound velocity value; a freeze button to instruct switching between a live mode and a freeze mode; a moving image playback button to instruct a moving image playback; and an analysis/measurement button to instruct the analysis/measurement of an ultrasonic image. The pointing device 204 is a device configured to accept an input of designation of a region on a screen of a display unit 104, for example, a track ball or a mouse. Here, it is also possible to use a touch panel as the pointing device 204.

A storage unit 102 is a storage apparatus configured to store a control program to control each block of the ultrasonic signal processing device 10 in the CPU 100, for example, a hard disk or a semiconductor memory.

The display unit 104 is, for example, a CRT (Cathode Ray Tube) display or a liquid crystal display. The display unit 104 performs display of ultrasonic images (moving image and still image) and display of various setting screens.

The ultrasonic probe 300 is a probe used by being touched to subject OBJ, and includes multiple ultrasonic transducers (elements) 302 forming a one-dimensional or two-dimensional transducer array. The ultrasonic transducer 302 transmits an ultrasonic beam to subject OBJ on the basis of a driving signal applied from a transmission circuit 402 while receiving an ultrasonic echo reflected from subject OBJ and outputting a detection signal.

The ultrasonic transducer 302 includes a vibrator configured such that electrodes are formed on both ends of a material (piezoelectric material) having piezoelectricity. As a piezoelectric material forming the above-mentioned vibrator, for example, it is possible to use a piezoelectric ceramic such as PZT (Pb (lead) zirconate titanate), and a polymer piezoelectric element such as PVDF (polyvinylidene difluoride). A piezoelectric material expands and contracts when a voltage is applied by transmitting an electrical signal to the electrodes of the above-mentioned vibrator, and an ultrasonic wave is generated in each vibrator by expansion and contraction of this piezoelectric material. For example, a pulsed ultrasonic wave is generated when a pulsed electrical signal is transmitted to the electrodes of the vibrator, and, an ultrasonic wave of continuous waves is generated when an electrical signal of continuous waves is transmitted to the electrodes of the vibrator. Further, the ultrasonic wave generated in each vibrator is synthesized and an ultrasonic beam is formed. Moreover, when an ultrasonic wave is received by each vibrator, the piezoelectric material of each vibrator expands and contracts to generate an electrical signal. The electrical signal generated in each vibrator is output to a reception circuit 404 as an ultrasonic detection signal.

Here, as the ultrasonic transducer 302, it is also possible to use multiple kinds of elements in different ultrasonic conversion schemes. For example, the vibrator configured by the above-mentioned piezoelectric material may be used as an element that transmits an ultrasonic wave, and an ultrasonic transducer (for example, Fabry-Perot resonator and fiber Bragg grating) of an optical detection scheme configured to convert an ultrasonic signal into an optical signal and detect it may be used as an element that receives the ultrasonic wave.

Ultrasonic diagnostic processing at a live mode is described. The live mode is a mode to display, analyze and measure an ultrasonic image (moving image) acquired by touching the ultrasonic probe 300 to subject OBJ and performing transmission and reception of ultrasonic waves.

When the ultrasonic probe 300 touches the subject OBJ and an ultrasonic diagnosis starts by an instruction input from the operation input unit 200, the CPU 100 outputs a control signal to a transmission/reception unit 400 and starts transmission of an ultrasonic beam to the subject OBJ and reception of an ultrasonic echo from the subject OBJ. The CPU 100 sets the transmission direction of the ultrasonic beam and the reception direction of the ultrasonic echo every ultrasonic transducer 302.

In addition, the CPU 100 selects a transmission delay pattern according to the transmission direction of the ultrasonic beam and selects a reception delay pattern according to the reception direction of the ultrasonic echo. Here, the transmission delay pattern is pattern data of a delay time given to a driving signal to form an ultrasonic beam in a desired direction with ultrasonic waves transmitted from multiple ultrasonic transducers 302. The reception delay pattern is pattern data of a delay time given to a detection signal to extract an ultrasonic echo from a desired direction by ultrasonic waves received by the multiple ultrasonic transducers 302. The above-mentioned transmission delay pattern and reception delay pattern are stored in the storage unit 102 beforehand The CPU 100 selects a transmission delay pattern and a reception delay pattern from the ones stored in the storage unit 102, and performs transmission/reception control of ultrasonic waves by outputting a control signal to the transmission/reception unit 400 according to the selected transmission delay pattern and reception delay pattern.

The transmission circuit 402 generates a driving signal according to the control signal from the CPU 100 and applies the driving signal to the ultrasonic transducer 302. At this time, the transmission circuit 402 delays the driving signal applied to each ultrasonic transducer 302 on the basis of the transmission delay pattern selected by the CPU 100 (transmission focus processing). Here, the transmission circuit 402 adjusts (delays) the timing at which the driving signal is applied to each ultrasonic transducer 302 such that ultrasonic waves transmitted from the multiple ultrasonic transducers 302 form an ultrasonic beam. Here, the timing at which the driving signal is applied may be adjusted such that the ultrasonic waves transmitted from the multiple ultrasonic transducers 302 at a time reach an entire imaging region of the subject OBJ.

The reception circuit 404 receives and amplifies the ultrasonic detection signal output from each ultrasonic transducer 302. As described above, since the distance between each ultrasonic transducer 302 and an ultrasonic reflection source in the subject OBJ varies, the time at which a reflection wave reaches each ultrasonic transducer 302 varies. The reception circuit 404 includes a delay circuit and delays each detection signal to the extent corresponding to the difference in the arrival time of the reflection wave (delay time), according to the sound velocity (assumed sound velocity) set according to the reception delay pattern selected by the CPU 100 or according to the distribution of the sound velocity. Further, the reception circuit 404 performs reception focus processing (beam forming) by performing matching addition on the detection signals to which the delay time is given. In a case where there is another ultrasonic reflection source in a position different from ultrasonic reflection source $X_{ROI}$, since the arrival time is different in an ultrasonic detection signal from another ultrasonic reflection source, the phase of the ultrasonic detection signal from another ultrasonic reflection source is negated by addition in an addition circuit of the reception circuit 404. By this means, a reception signal from ultrasonic reflection source $X_{ROI}$ becomes largest, and the focus is adjusted. By the above-mentioned reception focus processing, an acoustic ray signal (hereinafter referred to as "RF signal") in which the focus of an ultrasonic echo is narrowed is formed.

An A/D conversion unit 406 converts an analog RF signal output from the reception circuit 404 into a digital RF signal (hereinafter referred to as "RF data"). Here, the RF data includes phase information on a reception wave (carrier wave). The RF data output from the A/D conversion unit 406 is input in a signal processing unit 502 and a Raw data memory 602 respectively.

The Raw data memory 602 sequentially stores the RF data input from the AID conversion unit 406. Moreover, the Raw data memory 602 stores information on the frame rate input from the CPU 100 (for example, parameters showing a depth of an ultrasonic reflection position, a density of scanning lines and a visual field width) in association with the above-mentioned RF data.

The signal processing unit 502 applies envelope detection processing to the above-mentioned RF data after attenuation by the distance is corrected according to the depth of the ultrasonic reflection position by STC (Sensitivity Time gain Control), and generates B-mode image data (image data showing an amplitude of an ultrasonic echo by spot luminance (brightness)).

The B-mode image data generated by the signal processing unit 502 is acquired by a scanning scheme different from a scanning scheme for normal television signals. Therefore, a DSC (Digital Scan Converter) 504 converts the above-mentioned B-mode image data into normal image data (for example, image data of a television signal scanning scheme (NTSC (National Television System Committee) scheme) (raster conversion). An image processing unit 506 applies various kinds of necessary image processing (for example, gradation processing) to the image data input from the DSC 504.

The image memory 508 stores the image data input from the image processing unit 506. A D/A conversion unit 112 converts image data read out from the image memory 508 into an analog video signal and outputs it to the display unit 104. By this means, an ultrasonic image (moving image) taken by the ultrasonic probe 300 is displayed on the display unit 104.

Here, the focus line pitch of the ultrasonic transducer 302 (interval between elements of the transducer 302) and the line pitch of the display unit 104 (vertical line pitch) are not generally matched. For example, in a case where the focus line pitch is larger than the line pitch of the display unit 104, it is necessary to interpolate the image displayed on the display unit 104 by the use of the DSC 504.

Figure 2B:
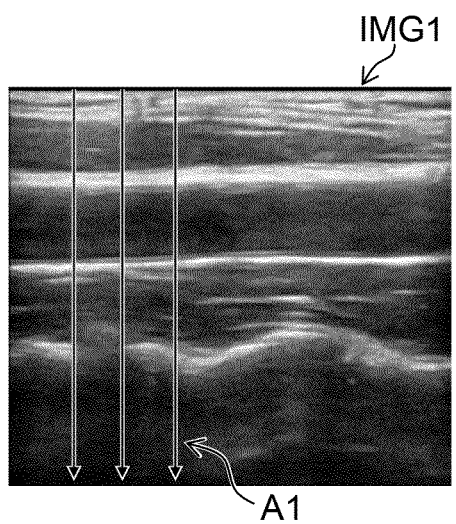
FIG. 2B is a diagram illustrating a relationship between an ultrasonic image acquired by the linear ultrasonic probe and an ultrasonic transmission line.

FIG. 2A is a diagram illustrating a linear ultrasonic probe, and FIG. 2B is a diagram illustrating a relationship between an ultrasonic image acquired by the linear ultrasonic probe and an ultrasonic transmission line.

As illustrated in FIG. 2A, ultrasonic transducers 302 are disposed in a one-dimensional (linear) manner in a linear ultrasonic probe 300A. Multiple ultrasonic transmission lines A1 output from the linear ultrasonic probe 300A are output from the element surface side of the ultrasonic probe 300A so as to be parallel to each other. As illustrated in FIG. 2B, a pitch of lines A1 transmitted from the linear ultrasonic probe 300A is larger than a vertical line pitch of ultrasonic image IMG1 displayed on the display unit 104. Therefore, in FIG. 2B, images between the lines A1 are interpolated by the DSC 504 and output to the display unit 104.

Figure 3A:
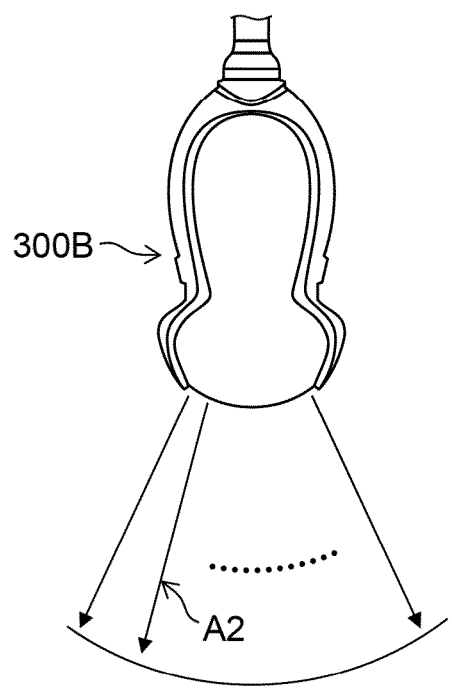
FIG. 3A is a diagram illustrating a convex ultrasonic probe.
Figure 3B:
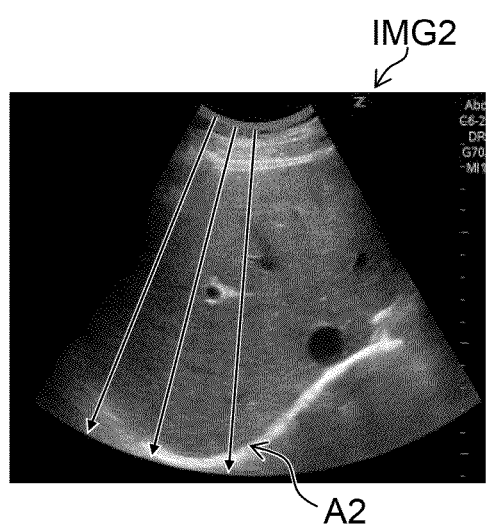
FIG. 3B is a diagram illustrating a relationship between an ultrasonic image acquired by the convex ultrasonic probe and an ultrasonic transmission line.

FIG. 3A is a diagram illustrating a convex ultrasonic probe, and FIG. 3B is a diagram illustrating a relationship between an ultrasonic image acquired by the convex ultrasonic probe and an ultrasonic transmission line.

As illustrated in FIG. 3A, the ultrasonic transducer 302 is disposed in a convex curved line shape with respect to subject OBJ in the convex ultrasonic probe 300B. Multiple ultrasonic transmission lines A2 output from the convex ultrasonic probe 300B are radially output from an element surface of the ultrasonic probe 300B. As illustrated in FIG. 3B, a pitch of lines A2 transmitted from the convex ultrasonic probe 300B is larger than a line pitch of ultrasonic image IMG2 displayed on the display unit 104. Therefore, in FIG. 3B, images between the lines A2 are interpolated by the DSC 504 and output to the display unit 104.

Here, the display unit 104 may be detachable from the ultrasonic signal processing device 10. In this case, the DSC 504 or the like can be configured to be installed on the display unit 104 instead of the ultrasonic signal processing device 10. Moreover, in a case where an image is output to an external display apparatus different from the ultrasonic signal processing device 10, it is also possible to install a scanning converter between the ultrasonic signal processing device 10 and the external display apparatus and perform interpolation processing according to a resolution of a monitor of the external display apparatus by the use of the scanning converter, without performing the interpolation processing in the DSC 504.

Here, a detection signal to which the reception focus processing is applied in the reception circuit 404 is assumed to be an RF signal in the present embodiment, but a detection signal to which the reception focus processing is not applied may be assumed to be the RF signal. In this case, multiple ultrasonic detection signals output from the multiple ultrasonic transducers 302 are amplified in the reception circuit 404, and RF data is generated by A/D conversion of the amplified detection signals, that is, RF signals in the A/D conversion unit 406. Further, the above-mentioned RF data is supplied to the signal processing unit 502 and stored in the Raw data memory 602. The reception focus processing is digitally performed in the signal processing unit 502.

Next, a moving image playback mode is described with reference to FIG. 1. The moving image playback mode is a mode configured to display, analyze and measure an ultrasonic diagnosis image on the basis of the RF data stored in the Raw data memory 602.

When a moving image playback button of the operator console 202 is pressed, the CPU 100 switches the operation mode of the ultrasonic signal processing device 10 to the moving image playback mode. At the moving image playback mode, the CPU 100 instructs the playback of RF data designated by an operation input from the operator, to a moving image playback unit 604. The moving image playback unit 604 reads out the RF data from the Raw data memory 602 according to the instruction from the CPU 100 and transmits it to the signal processing unit 502 in an image signal generation unit 500. After the RF data transmitted from the Raw data memory 602 is subjected to predetermined processing (processing similar to that at the live mode) and converted into image data in the signal processing unit 502, the DSC 504 and the image processing unit 506, and it is output to the display unit 104 through the image memory 508 and the D/A conversion unit 112. By this means, an ultrasonic image (moving image or still image) according to the RF data stored in the Raw data memory 602 is displayed on the display unit 104.

If the freeze button of the operator console 202 is pressed when an ultrasonic image (moving image) is displayed at the live mode or the moving image playback mode, an ultrasonic image displayed when the freeze button is pressed is subjected to still image display in the display unit 104. By this means, the operator can display and observe the still image of ROI (Region of Interest).

When a measurement button of the operator console 202 is pressed, analysis and measurement designated by an operation input from the operator are performed. In a case where the measurement button is pressed at each operation mode, a data analysis unit 106 acquires RF data before image processing is applied, from the A/D conversion unit 406 or the Raw data memory 602, and performs analysis/measurement (for example, strain analysis of an organization part (hardness diagnosis), measurement of a blood flow, movement measurement of the organization part or IMT (Intima-Media Thickness) value measurement) designated by the operator using the RF data. The analysis/measurement result by the data analysis unit 106 is output to the DSC 504 of the image signal generation unit 500. The DSC 504 inserts the analysis/measurement result by the data analysis unit 106 in image data of an ultrasonic image and outputs it to the display unit 104. By this means, the ultrasonic image and the analysis/measurement result are displayed on the display unit 104.

The data analysis unit 106 calculates the optimal sound velocity value and the local sound velocity value every region in the subject OBJ on the basis of the RF data output from the transmission/reception unit 400.

Here, for example, the optimal sound velocity value is calculated as a sound velocity value in which at least one of the contrast and sharpness of an image in the region of interest (ROI) in subject OBJ becomes highest in a B-mode image. That is, the optimal sound velocity value corresponds to the average sound velocity value in a region from the ultrasonic probe 300 to the above-mentioned region of interest, and denotes a virtual sound velocity value calculated by performing reception focus.

Moreover, the local sound velocity value is a sound velocity value in the above-mentioned region of interest calculated using the above-mentioned optimal sound velocity value.

Figure 4A:
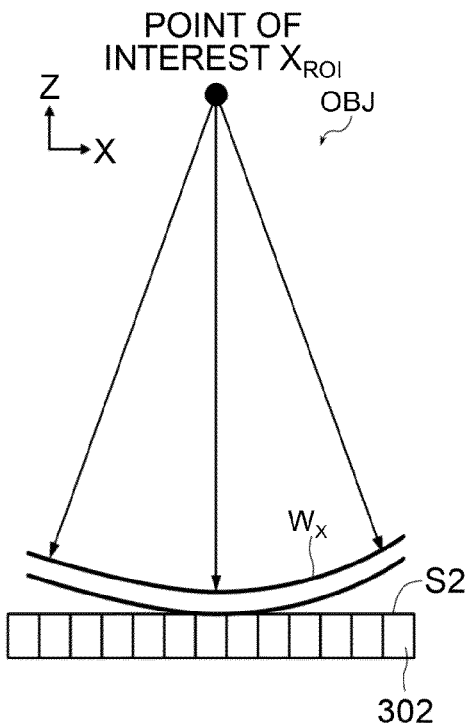
FIG. 4A is a diagram schematically illustrating a reception wave received when a point of interest is assumed to be a reflection point.
Figure 4B:
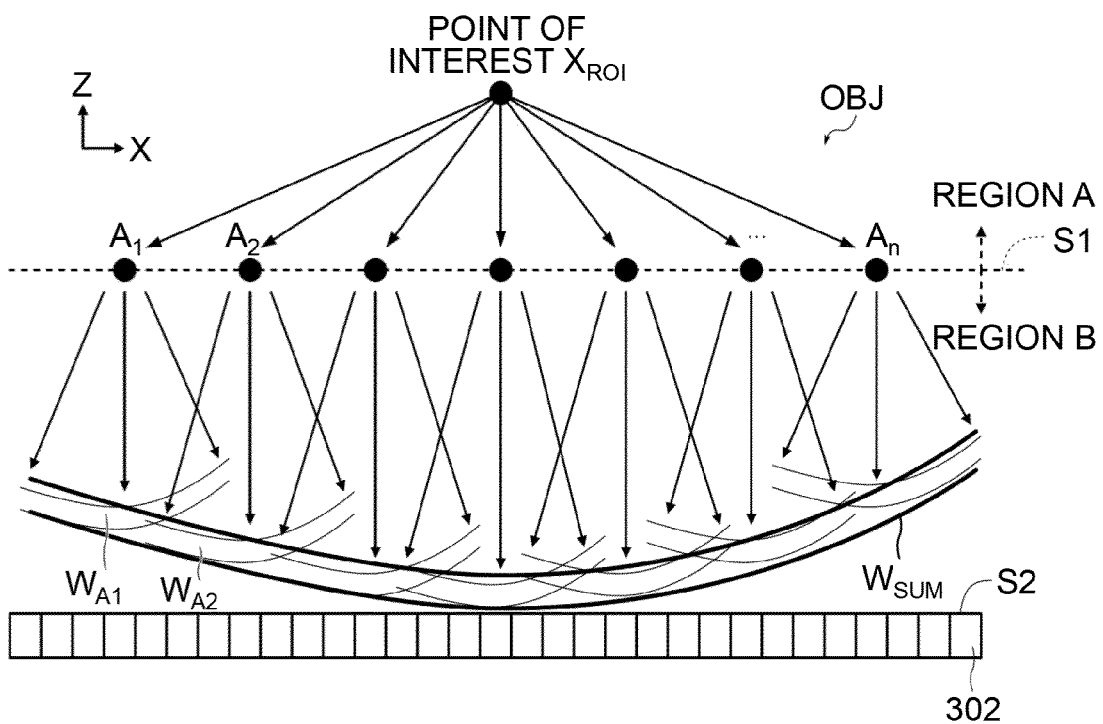
FIG. 4B is a diagram schematically illustrating a synthetic reception wave acquired by synthesizing reception waves propagated from the point of interest and received through a point between the point of interest and an ultrasonic probe.

FIGS. 4A and 4B are diagrams schematically illustrating calculation processing of the local sound velocity value according to the present embodiment. In FIGS. 4A and 4B, the X axis shows the scan direction (array direction of elements 302) and the Z axis shows the depth direction in the subject OBJ. It is assumed that both sound velocity Va in region A between a point of interest $X_{ROI}$ and points A1, A2, . . . , An in FIG. 4B and sound velocity Vb in region B between points A1, A2, . . . , An and the ultrasonic probe 300 are constant. Here, in FIG. 4B, boundary S1 between region A and region B has a straight shape, but it may have a curved shape or an irregular shape.

Reception wave $W_x$ illustrated in FIG. 4A denotes a reception wave received when the point of interest $X_{ROI}$ is assumed to be a reflection point, on the basis of the optimal sound velocity value in the point of interest $X_{ROI}$ (calculation object of the local sound velocity value).

Synthetic reception wave $W_{SUM}$ illustrated in FIG. 4B denotes a synthetic reception wave acquired by synthesizing reception waves ($W_{A1}$, $W_{A2}$, . . . , $W_{An}$) that are ultrasonic waves propagated from the point of interest $X_{ROI}$ and received through points A1, A2, . . . , An. When the distances from the point of interest $X_{ROI}$ to points A1, A2, . . . , An are $X_{ROI}$A1, $X_{ROI}$A2, . . . , $X_{ROI}$An respectively, the times that elapse before an ultrasonic wave from the point of interest $X_{ROI}$ reaches points A1, A2, . . . , An are $X_{ROI}$A1/Va, $X_{ROI}$A2/Va, $X_{ROI}$An/Va respectively. Moreover, waveforms of the reception waves when the ultrasonic waves generated from points A1, A2, . . . An reach element surface S2 of the ultrasonic probe 300 are calculated on the basis of the optimal sound velocity value at each point. Synthetic reception wave $W_{SUM}$ can be calculated by synthesizing reflection waves (ultrasonic echoes) generated from points A1, A2, . . . , An with delays $X_{ROI}$A1/Va, $X_{ROI}$A2/Va, . . . , $X_{ROI}$An/Va respectively.

According to the Huygens' principle, reception wave $W_x$ and synthetic reception wave $W_{SUM}$ are matched. Therefore, sound velocity value Va in which the difference between reception wave $W_x$ and synthetic reception wave $W_{SUM}$ becomes minimum is assumed to be a local sound velocity value in the point of interest $X_{ROI}$ (region A). For example, the difference between reception wave $W_x$ and synthetic reception wave $W_{SUM}$ is calculated by a method of finding cross-correlation of the reception waveform or reception time in each element 302 with respect to reception wave $W_x$ and synthetic reception wave $W_{SUM}$ or the like.

Here, the region from the ultrasonic probe 300 to the point of interest $X_{ROI}$ is divided into regions of two layers in the Z direction and the local sound velocity value is calculated in the examples illustrated in FIGS. 4A and 4B, but the presently disclosed subject matter is not limited to this. For example, it may be divided into regions of three or more layers in the Z direction and the local sound velocity value may be calculated in order from the layer on the side of the ultrasonic probe 300. Moreover, the local sound velocity value may be calculated assuming multiple regions in which the optimal sound velocity values are mutually different in the X direction.

A sound velocity map creation unit 108 generates an image signal showing a sound velocity image (sound velocity map) that displays sound velocity distribution in the subject, on the basis of calculation in the data analysis unit 106. A display control unit 110 selects at least one of the B-mode image signal generated by the image signal generation unit 500 and the image signal showing the sound velocity map generated by the sound velocity map creation unit 108, according to operator's operation using the operator console 202, and generates an image signal for display. This image signal for display is output by the D/A conversion unit 112 as an analog image signal and thereafter output to the display unit 104.

When the display mode switching button is pressed, the display mode is switched among a mode to display a B-mode image alone, a mode to superimpose and display the determination result of a local sound velocity value over the B-mode image (for example, display in which color classification or brightness is changed according to the local sound velocity value or display in which points of the identical local sound velocity value are connected by a line) and a mode to display the B-mode image and an image of the determination result of the local sound velocity value at the same time (Dual). By this means, for example, the operator can discover a lesion by observing the determination result of the local sound velocity value.

Here, according to the determination result of the local sound velocity value, a B-mode image acquired by performing at least one of transmission focus processing and reception focus processing may be displayed on the display unit 104. Moreover, an optimal sound velocity value image subjected to two-dimensional imaging of the optimal sound velocity value or a local sound velocity value image subjected to two-dimensional imaging of the local sound velocity value may be displayed on the display unit 104. Moreover, the B-mode image (ultrasonic image) and the optimal sound velocity value image or the local sound velocity value image may be arranged side-by-side thereon or overlapped, and displayed. Moreover, the operation input unit 200 may allow the operator to select images to be arranged side-by-side or overlapped, and displayed.

First Embodiment of Ultrasonic Scan

FIG. 5 is a diagram schematically illustrating ultrasonic scan processing according to the first embodiment of the presently disclosed subject matter. In FIG. 5, the X axis shows the scanning direction. In the example illustrated in FIG. 5, the number of transmission focus lines (scanning line number) to generate an ultrasonic image (B-mode image) for one frame is assumed to be 240 lines.

As illustrated in FIG. 5, in the present embodiment, a scan for measurement of the optimal sound velocity value is performed only in line L(5n+1) (n=0, 1, . . . , 47) among 240 scanning lines (B measurement lines) L(1), . . . , L(240) for creating a B-mode image. That is, the scanning is performed while changing the sound velocity value at the time of scanning of optimal sound velocity measurement lines L(5n+1) (n=0, 1, . . . , 47), and the optimal sound velocity value in a scanning range is calculated at the same time as creation of the B-mode image. Further, at the time of scanning of four B measurement lines L(5n+2), L(5n+3), L(5n+4) and L(5n+5) among the optimal sound velocity measurement lines, beam forming is performed using the optimal sound velocity value calculated by scanning of previously-scanned optimal sound velocity measurement line L(5n+1), and a B-mode image is created by the image signal generation unit 500.

Figure 6:
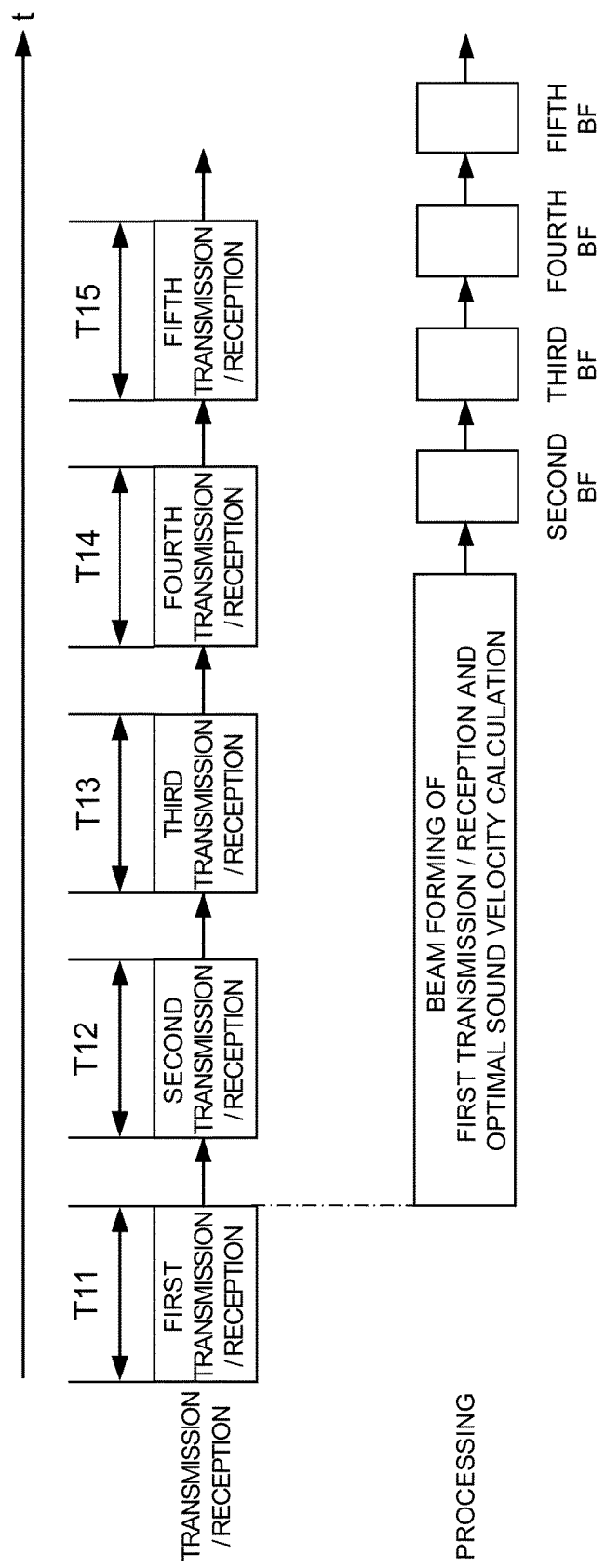
FIG. 6 is a timing chart illustrating execution timings of ultrasonic transmission and reception and ultrasonic signal processing.

FIG. 6 is a timing chart showing execution timings of ultrasonic transmission and reception and ultrasonic signal processing. In FIG. 6, T11, T12, . . . , T15 are amounts of time required for transmission and reception of lines L(5n+1), L(5n+2), L(5n+3), L(5n+4) and L(5n+5) respectively.

As illustrated in FIG. 6, when the transmission and reception of optimal sound velocity measurement line L(5n+1) end, subsequently, the transmission and reception of B measurement lines L(5n+2), L(5n+3), L(5n+4) and L(5n+5), optimal sound velocity measurement line L(5(n+1)+1) and B measurement lines L(5(n+1)+2) and L(5(n+1)+3), . . . , are sequentially executed.

When the transmission and reception of optimal sound velocity measurement line L(5n+1) end, the CPU 100 performs beam forming according to optimal sound velocity measurement line L(5n+1) and calculates the optimal sound velocity value of each depth in a scanning range of optimal sound velocity measurement line L(5n+1) by the data analysis unit 106. Further, in a case where beam forming of ultrasonic detection signals received by scanning of B measurement lines L(5n+2), L(5n+3), L(5n+4) and L(5n+5) is performed, sound velocity correction is performed using the optimal sound velocity value of each depth calculated on the basis of optimal sound velocity measurement line L(5n+1).

Further, when similar processing is repeated even at the time of transmission and reception of subsequent optimal sound velocity measurement line L(5(n+1)+1) and B measurement lines L(5(n+1)+2) and L(5(n+1)+3), . . . , a B-mode image for one frame is created by the image signal generation unit 500 and a sound velocity map showing the distribution of optimal sound velocity values is created by the sound velocity map creation unit 108. Moreover, by calculating local sound velocity values in the subject OBJ by the use of the above-mentioned optimal sound velocity values, a sound velocity map showing the distribution of the local sound velocity values is created. These B-mode image and sound velocity map are displayed on the display unit 104 according to a display mode set by the operation input unit 200.

According to the present embodiment, by assigning an optimal sound velocity measurement line to only a part of B measurement lines, it is possible to reduce the time lag between the creation of a B-mode image and the calculation of an optimal sound velocity value as compared with a case where the B measurement lines are scanned after a transmission line for sound velocity correction is scanned for one frame. By this means, it is possible to calculate and display the optimal sound velocity value and the local sound velocity value in real time while displaying the B-mode image. Moreover, as illustrated in FIG. 6, since it is possible to effectively operate processors for calculation (the CPU 100, the data analysis unit 106, the sound velocity map creation unit 108 and the image signal generation unit 500), it becomes possible to shorten the processing time required for beam forming and the calculation of the optimal sound velocity value, and so on.

Figure 7:
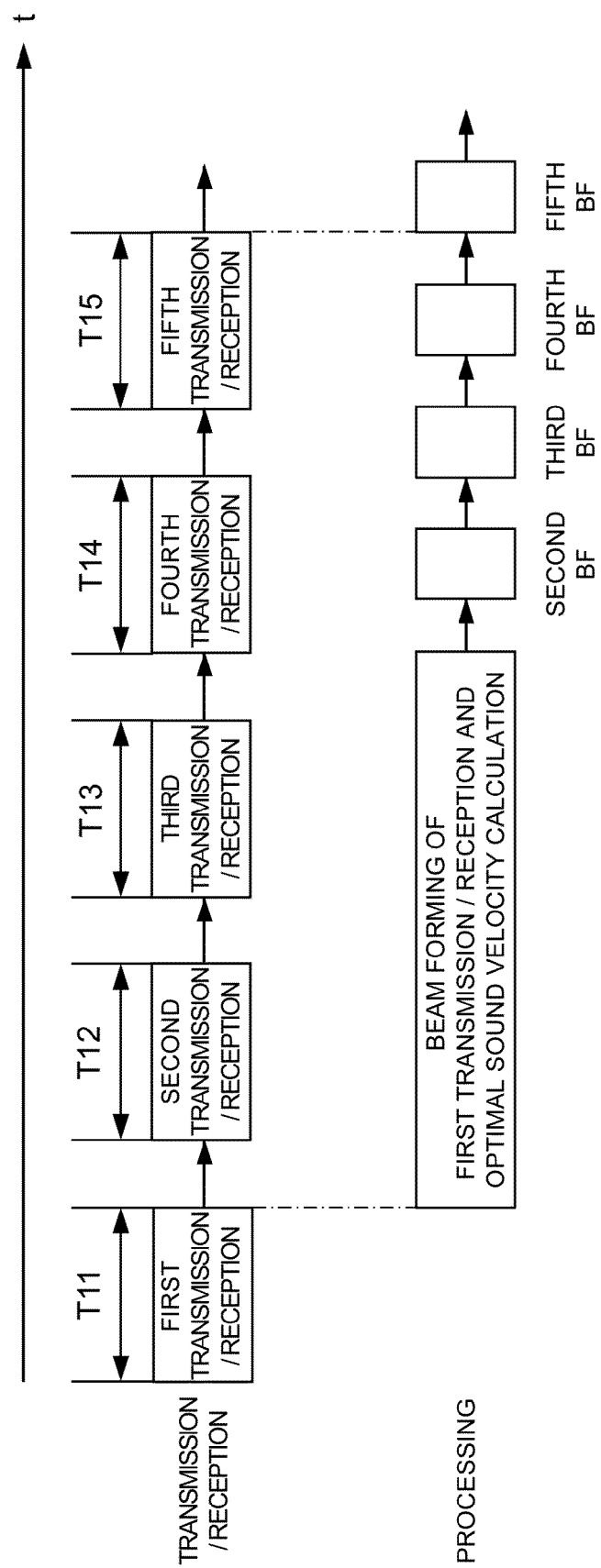
FIG. 7 is a timing chart illustrating another example of the execution timings of the ultrasonic transmission and reception and the ultrasonic signal processing.

Here, it is preferable to decide the number of B measurement lines for which sound velocity value calculation is not performed (4 lines from L(5n+2) to L(5n+5) in the present embodiment) on the basis of the first beam forming time, the calculation time of optimal sound velocity value calculation and second or subsequent beam forming time. For example, the number of B measurement lines is decided such that the end timing of transmission and reception time of the last B measurement line (line immediately before the optimal sound velocity measurement line) and the start timing of beam forming based on the last B measurement line are substantially matched. In the present embodiment, as illustrated in FIG. 7, the end timing of transmission and reception time T15 of B measurement line L(5n+5) and the start timing of the fifth beam forming time are matched. By deciding the number of B measurement lines as described above, it becomes possible to further shorten the processing time required for beam forming and calculation of the optimal sound velocity value, and so on.

Here, in a case where the sound velocity map creation unit 108 calculates the optimal sound velocity values in the positions of B measurement lines L(5n+2), L(5n+3), L(5n+4) and L(5n+5), they may be calculated by interpolation using an optimal sound velocity value calculated by optimal sound velocity measurement line L(5n+1), or an optimal sound velocity value calculated by optimal sound velocity measurement lines L(5n+1) and L(5(n+1)+1).

Second Embodiment

Next, the second embodiment of the presently disclosed subject matter is described. Here, in the following explanation, explanation is omitted about the configuration similar to the above-mentioned first embodiment.

Figure 8:
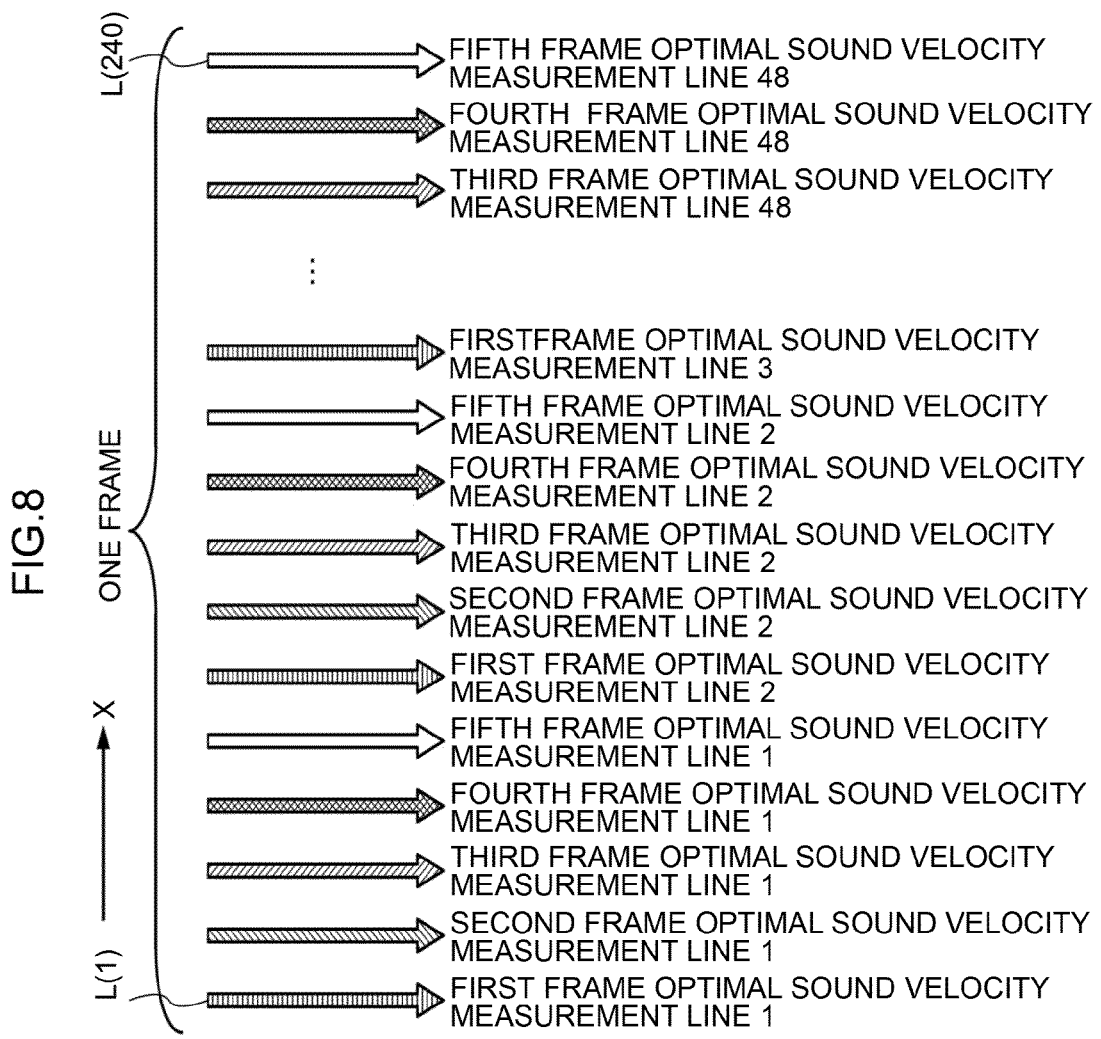
FIG. 8 is a diagram schematically illustrating ultrasonic scan processing according to the second embodiment of the presently disclosed subject matter.

FIG. 8 is a diagram schematically illustrating ultrasonic scan processing according to the second embodiment of the presently disclosed subject matter. In FIG. 8, the X axis shows the scanning direction. In the example illustrated in FIG. 8, the number of scanning lines to generate an ultrasonic image (B-mode image) for one frame is assumed to be 240 lines.

In the present embodiment, the assignment of optimal sound velocity measurement lines is changed every frame. As illustrated in FIG. 8, the optimal sound velocity measurement lines are assigned to L(5n+1) (n=0, 1, . . . , 47) (transmission line set for a frame F1) at the time of the scan of the first frame F1, L(5n+2) (n=0, 1, . . . , 47) (transmission line set for a frame F2) at the time of the scan of the second frame F2, L(5n+3) (n=0, 1, . . . , 47) (transmission line set for a frame F3) at the time of the scan of the third frame F3, L(5n+4) (n=0, 1, . . . , 47) (transmission line set for a frame F4) at the time of the scan of the fourth frame F4, and L(5n+5) (n=0, 1, . . . , 47) (transmission line set for a frame F5) at the time of the scan of the fifth frame F5.

Further, the optimal sound velocity measurement lines are assigned to lines L(5n+1) (n=0, 1, . . . , 47) at the time of the scan of the sixth frame F6, and the assignment of the optimal sound velocity measurement lines (transmission line set) is repeated in the above-mentioned order after the sixth frame F6.

In the present embodiment, similar to the above-mentioned first embodiment, it is possible to calculate and display the optimal sound velocity value and the local sound velocity value in real time while displaying a B-mode image.

Here, in this embodiment, the optimal sound velocity value calculated at the time of taking an image of the B mode of each frame may be held in a RAM or the like of the storage unit 102 and used at the time of display of a subsequent frame. Specifically, the optimal sound velocity value calculated at the scan time of the first frame F1 is held until the scan time of the first to fifth frames F1 to F5, and the optimal sound velocity value calculated at the scan time of the second frame F2 is held until the scan time of the second to sixth frames F2 to F6 (that is, in a case where the assignment interval of optimal sound velocity measurement lines is assumed to be k, the measurement result of optimal sound velocity is held while the scan of k frames is executed). Thus, the optimal sound velocity value is rewritten in order of frame imaging. Further, a sound velocity map created from the held optimal sound velocity values by the sound velocity map creation unit 108 is added. By this means, it becomes possible to create a sound velocity image with higher resolution over the entire scan range.

Figure 9:
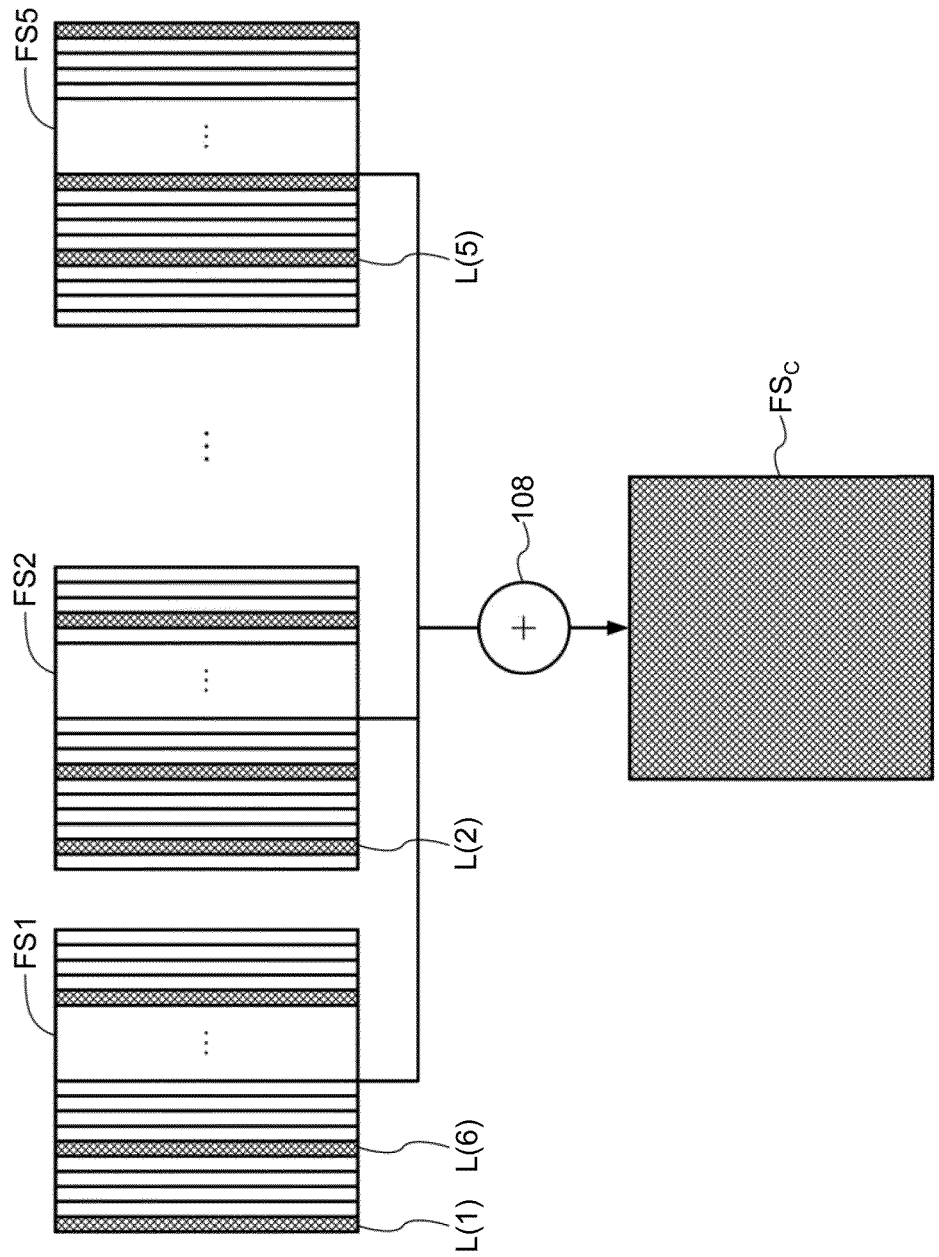
FIG. 9 is a diagram to describe addition processing of a sound velocity map.

As illustrated in FIG. 9, in a sound velocity map FS1 of the optimal sound velocity value acquired at the scan time of the frame F1, the sound velocity is illustrated only in the position of the optimal sound velocity measurement line L(5n+1) (n=0, 1, . . . , 47) (for example, by gradation). Similarly, in sound velocity maps FS2 to FS5 of the optimal sound velocity values acquired at the scan time of the frames F2 to F5, the sound velocity is illustrated only in the position of the optimal sound velocity measurement lines L(5n+2) to L(5n+5) respectively. By adding the sound velocity maps FS1 to FS5 illustrated in FIG. 9, a sound velocity map $FS_C$ of the entire scan range is created. By this means, it becomes possible to display a sound velocity map $FS_C$ of the entire scan range at the display time of a B-mode image after the frame F5.

Further, when a sound velocity map FS6 corresponding to the sixth frame F6 is created, the frame F1 is replaced with F6 and a sound velocity image is created by addition processing of the sound velocity maps F6 and F2 to F5. Such a sound velocity map $FS_C$ has advantages that the resolution of the sound velocity display is higher and the time lag with a B-mode image is smaller.

Third Embodiment

Next, the third embodiment of the presently disclosed subject matter is described. Here, in the following explanations, explanation is omitted about the configuration similar to the above-mentioned first embodiment.

Figure 10:
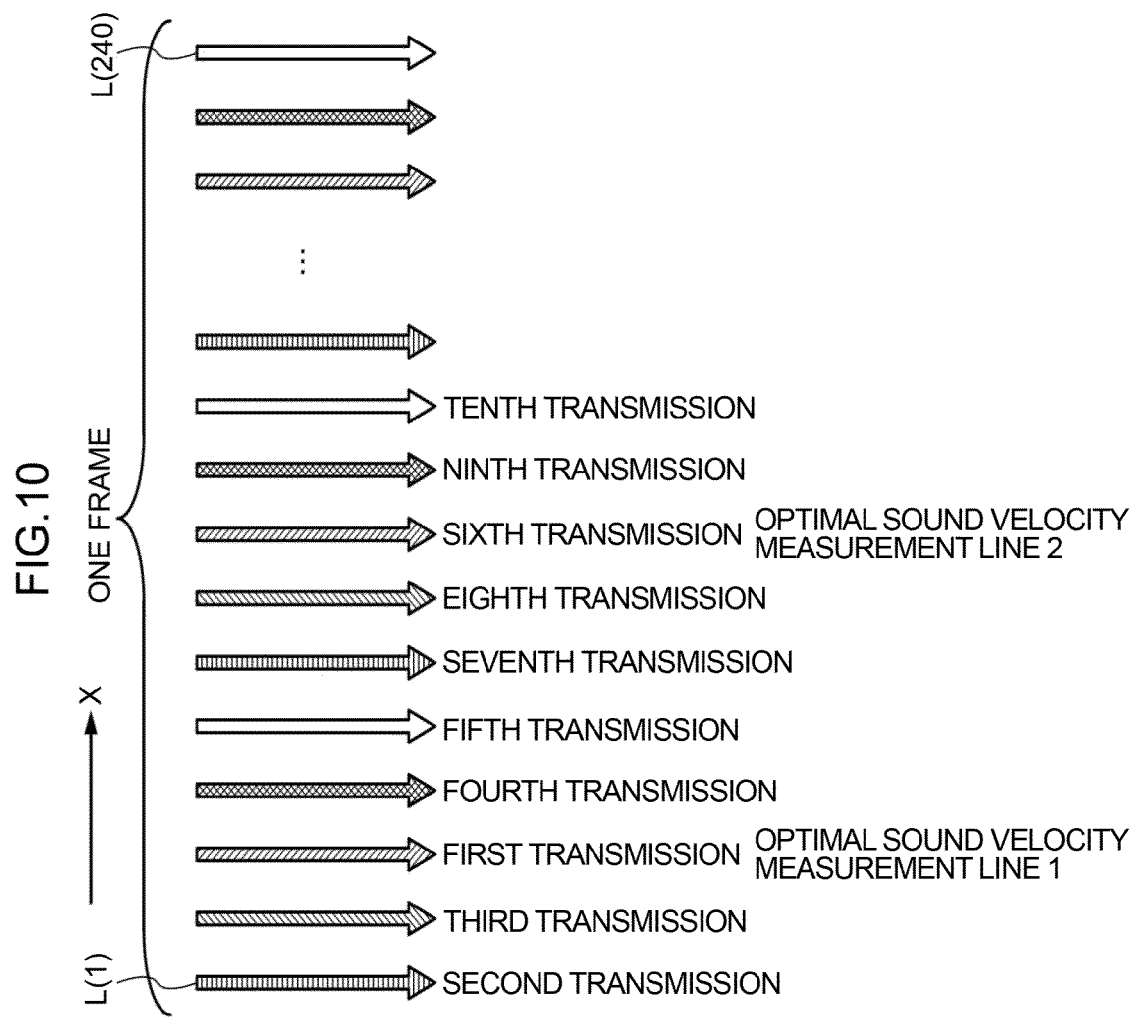
FIG. 10 is a diagram schematically illustrating ultrasonic scan processing according to the third embodiment of the presently disclosed subject matter.

FIG. 10 is a diagram schematically illustrating an ultrasonic scan processing according to the third embodiment of the presently disclosed subject matter. In FIG. 10, the X axis shows the scanning direction. In the example illustrated in FIG. 10, the number of scanning lines to generate an ultrasonic image (B-mode image) for one frame is assumed to be 240 lines.

In the present embodiment, an optimal sound velocity measurement line is assigned to a line L(5n+3) (n=0, 1, . . . , 47).

In the present embodiment, first, transmission and reception are performed in the optimal sound velocity measurement line L(5n+3) (n=0, 1, . . . , 47), and the optimal sound velocity value is calculated by the data analysis unit 106.

Next, in parallel to the calculation of the optimal sound velocity value, transmission and reception of ultrasonic waves in B measurement lines L(5n+1), L(5n+2), L(5n+4) and L(5n+5) are sequentially performed. Further, beam forming in the B measurement lines L(5n+1), L(5n+2), L(5n+4) and L(5n+5) are performed using the optimal sound velocity value calculated in the optimal sound velocity measurement line L(5n+3).

By sequentially repeating the above-mentioned processing with respect to n=0, 1, . . . , 47, a B-mode image for one frame is acquired.

Even in the present embodiment, similar to the above-mentioned first and second embodiments, it is possible to calculate and display the optimal sound velocity value and the local sound velocity value in real time while displaying the B-mode image.

Figure 11:
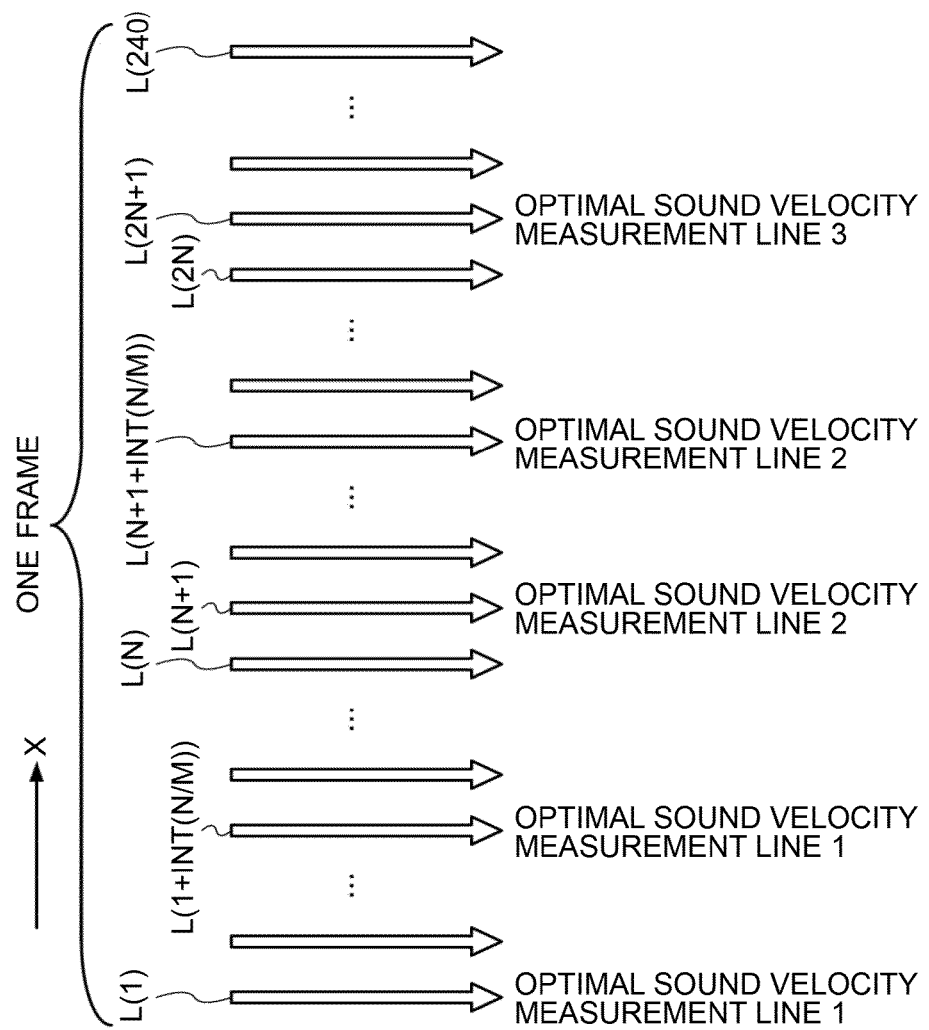
FIG. 11 is a diagram schematically illustrating ultrasonic scan processing in a case where M (M is an integer equal to or greater than 1 and less than N) lines of N (N is an integer equal to or greater than 2) transmission focus lines are assumed to be sound velocity measurement lines.

Here, the number of sound velocity measurement lines is one every five transmission focus lines in each above-mentioned embodiment, the presently disclosed subject matter is not limited to this. M (M is an integer equal to or greater than 1 and less than N) lines of N (N is an integer equal to or greater than 2) transmission focus lines may be assumed to be sound velocity measurement lines. In this case, the sound velocity measurement lines can be equally distributed in the N transmission focus lines. For example, as illustrated in FIG. 11, it is possible to dispose the sound velocity measurement line every integral part of N/M (hereafter referred to as INT(N/M)). Moreover, the disposition density of sound velocity measurement lines may be able to be manually set by the user by the operation input unit 200 or the pointing device 204, and so on.

Even in the example of FIG. 11, as described in the second embodiment, it is possible to change the assignment of the optimal sound velocity measurement lines every frame. In a case where the optimal sound velocity measurement line is disposed every INT(N/M), the optimal sound velocity measurement lines may be assumed to be lines L(Nn+1), L(Nn+1+INT(N/M)) and L(Nn+1+2×INT(N/M)), . . . (n=0, 1, . . . , 47; INT(N/M)<N) (transmission line set with respect to a frame F1) at the scan time of the first frame F1, the optimal sound velocity measurement lines may be assumed to be lines L(Nn+2), L(Nn+2+INT(N/M)) and L(Nn+2+2×INT (N/M)), . . . (n=0, 1, . . . , 47; INT(N/M)<N) (transmission line set with respect to a frame F2) at the scan time of the second frame F2, and the optimal sound velocity measurement lines may be assumed to be lines L(Nn+i), L(Nn+i+INT(N/M)) and L(Nn+i+2×INT(N/M)), . . . (n=0, 1, . . . , 47; INT(N/M) <N; i<N) (transmission line set with respect to a frame F1) at the scan time of the i-th frame Fi.

Moreover, even in the example of FIG. 11, as described in the third embodiment, it is possible to set the disposition of optimal sound velocity measurement lines and the transmission and reception order of lines.

An ultrasonic wave is transmitted once every transmission focus line (optimal sound velocity measurement line and B measurement line) in each above-mentioned embodiment, but the presently disclosed subject matter is not limited to this. For example, even in a case where transmission multi-focus to transmit an ultrasonic wave multiple times every transmission focus line, the ultrasonic signal processing method according to each above-mentioned embodiment is applicable. Moreover, in a case where the transmission multi-focus is performed, for example, the transmission multi-focus may be performed only on the optimal sound velocity measurement lines.

Here, the assignment interval of optimal sound velocity measurement lines is not limited to five lines. The assignment interval of the optimal sound velocity measurement lines may be decided according to the throughput of the CPU 100 or the operation situation of the CPU 100. For example, the assignment interval of the optimal sound velocity measurement lines may be narrowed as the throughput of the CPU 100 is higher or the utilization of the CPU 100 is lower.

Moreover, the assignment interval of the optimal sound velocity measurement lines may not be constant. For example, by performing an operation input from the operation input unit 200, the operator may be possible to set the interval of the optimal sound velocity measurement lines while seeing a B-mode image and a sound velocity map.

Here, each above-mentioned embodiment shows an example of linear scan, but the presently disclosed subject matter is not limited to this. That is, even in a case where convex or sector scan is implemented, by assigning optimal sound velocity measurement lines into B measurement lines at regular intervals, the ultrasonic scan processing of the present embodiment is applicable.

What is claimed is:
1. An ultrasonic signal processing device comprising:
an ultrasonic probe including multiple elements configured to transmit an ultrasonic wave to a subject, receive an ultrasonic wave reflected by the subject and output an ultrasonic detection signal;

a transmission/reception data acquisition unit configured to acquire transmission/reception data by controlling the ultrasonic probe, sequentially transmitting an ultrasonic wave into the subject along multiple transmission focus lines and receiving the ultrasonic wave reflected by the subject; and a sound velocity measurement unit configured to measure sound velocity in the subject according to transmission/reception data acquired in ultrasonic transmission of M times (M is an integer equal to or greater than 1 and less than N) along different transmission focus lines among ultrasonic transmission of N times (N is an integer equal to or greater than 2) along the multiple transmission focus lines when ultrasonic transmission is sequentially performed at least one time on each of the multiple transmission focus lines to create an ultrasonic image for one frame.

2. The ultrasonic signal processing device according to claim 1, further comprising:

an ultrasonic image creation unit configured to create an ultrasonic image in the subject according to the transmission/reception data acquired by the transmission/reception data acquisition unit; and a display unit configured to display the ultrasonic image.

3. The ultrasonic signal processing device according to claim 2, wherein, when the ultrasonic image creation unit creates an ultrasonic image of N consecutive frames, the sound velocity measurement unit makes positions of transmission focus lines for a measurement of the sound velocity in the subject different every frame.

4. The ultrasonic signal processing device according to claim 3, further comprising:

a sound velocity holding unit configured to hold a sound velocity for the N frames measured when the ultrasonic image for the N consecutive frames is created by the ultrasonic image creation unit, at least while the ultrasonic image for the N frames is created and displayed; and a sound velocity image creation unit configured to create a sound velocity image showing a sound velocity distribution in the subject by complementing the sound velocity for the N frames held in the sound velocity holding unit.

5. The ultrasonic signal processing device according to claim 4, wherein the sound velocity image creation unit creates an optimal sound velocity value image showing an optimal sound velocity value in the subject and a local sound velocity value image showing a local sound velocity value of each region in the subject by complementing the sound velocity for the N frames held in the sound velocity holding unit.

6. The ultrasonic signal processing device according to claim 4, wherein the display unit displays the sound velocity image together with the ultrasonic image according to an operation input from an operator.

7. The ultrasonic signal processing device according to claim 5, wherein, according to an operation input from an operator, the display unit selects and displays at least one of an optimal sound velocity value image subjected to a two-dimensional imaging of an optimal sound velocity value, a local sound velocity value image subjected to a two-dimensional imaging of a local sound velocity value every region in the subject, and the ultrasonic image.

8. The ultrasonic signal processing device according to claim 1, wherein:

the sound velocity measurement unit calculates an optimal sound velocity value in the subject according to the transmission/reception data acquired in the ultrasonic transmission of M times; and the transmission/reception data acquisition unit performs beam forming during the ultrasonic transmission and reception of N times.

9. The ultrasonic signal processing device according to claim 1, wherein the transmission/reception data acquisition unit calculates a line between transmission lines of the M times by interpolation operation, using a pixel value acquired according to the transmission/reception data acquired by the ultrasonic transmission of M times.

10. The ultrasonic signal processing device according to claim 1, wherein the sound velocity is an optimal sound velocity value or a local sound velocity value.

11. The ultrasonic signal processing device according to claim 1, wherein the sound velocity measurement unit measures a local sound velocity value of each region in the subject according to an optimal sound velocity value in the subject.

12. An ultrasonic signal processing method comprising:

a transmission/reception data acquisition step of acquiring transmission/reception data, by controlling an ultrasonic probe including multiple elements configured to transmit an ultrasonic wave to a subject, receive an ultrasonic wave reflected by the subject and output an ultrasonic detection signal, sequentially transmitting an ultrasonic wave into the subject along multiple transmission focus lines and receiving the ultrasonic wave reflected by the subject; and a sound velocity measurement step of measuring sound velocity in the subject according to transmission/reception data acquired in ultrasonic transmission of M times (M is an integer equal to or greater than 1 and less than N) along different transmission focus lines among ultrasonic transmission of N times (N is an integer equal to or greater than 2) along the multiple transmission focus lines when ultrasonic transmission is sequentially performed at least one time on each of the multiple transmission focus lines to create an ultrasonic image for one frame.

13. The ultrasonic signal processing method according to claim 12, further comprising:

an ultrasonic image creation step of creating an ultrasonic image in the subject according to the transmission/reception data acquired in the transmission/reception data acquisition step; and a display step of displaying the ultrasonic image on a display unit.

14. The ultrasonic signal processing method according to claim 13, wherein, when an ultrasonic image of N consecutive frames is created in the ultrasonic image creation step, positions of transmission focus lines for a measurement of the sound velocity in the subject are made different every frame in the sound velocity measurement step.

15. The ultrasonic signal processing method according to claim 14, further comprising:

a sound velocity holding step of holding a sound velocity for the N frames measured when the ultrasonic image for the N consecutive frames is created in the ultrasonic image creation step, at least while the ultrasonic image for the N frames is created and displayed; and a sound velocity image creation step of creating a sound velocity image showing a sound velocity distribution in the subject by complementing the sound velocity for the N frames held in the sound velocity holding step.

16. The ultrasonic signal processing method according to claim 15, wherein, in the sound velocity image creation step, an optimal sound velocity value image showing an optimal sound velocity value in the subject and a local sound velocity value image showing a local sound velocity value of each region in the subject are created by complementing the sound velocity for the N frames held in the sound velocity holding step.

17. The ultrasonic signal processing method according to claim 15, further comprising a step of displaying the sound velocity image together with the ultrasonic image by the display unit according to an operation input from an operator.

18. The ultrasonic signal processing method according to claim 16, wherein, according to an operation input from an operator, the display unit selects and displays at least one of an optimal sound velocity value image subjected to a two-dimensional imaging of an optimal sound velocity value, a local sound velocity value image subjected to a two-dimensional imaging of a local sound velocity value every region in the subject, and the ultrasonic image.

19. The ultrasonic signal processing method according to claim 12, wherein:

an optimal sound velocity value in the subject is calculated according to the transmission/reception data acquired in the ultrasonic transmission of M times in the sound velocity measurement step; and beam forming is performed during the ultrasonic transmission and reception of N times in the transmission/reception data acquisition step.

20. The ultrasonic signal processing method according to claim 12, wherein, in the transmission/reception data acquisition step, a line between transmission lines of the M times is calculated by interpolation operation, using a pixel value acquired according to the transmission/reception data acquired by the ultrasonic transmission of M times.

* * * * *